United States Patent
Nishimura et al.

[11] Patent Number: 6,013,492
[45] Date of Patent: *Jan. 11, 2000

[54] MICROBIAL PROCESS FOR PRODUCING CALCIUM D-PANTOTHENATE

[75] Inventors: Sunao Nishimura, Kakogawa; Hiroshi Miki, Kobe; Junichi Matsumoto; Kosaku Shibutani, both of Kakogawa; Hideo Yada, Settsu, all of Japan

[73] Assignee: Takeda Chemical Industries, Ltd., Osaka, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/647,903

[22] PCT Filed: Apr. 10, 1996

[86] PCT No.: PCT/JP96/00976

§ 371 Date: Jun. 4, 1996

§ 102(e) Date: Jun. 4, 1996

[87] PCT Pub. No.: WO96/33283

PCT Pub. Date: Oct. 24, 1996

[30] Foreign Application Priority Data

Apr. 21, 1995 [JP] Japan .................................. 7-097268

[51] Int. Cl.⁷ .............................. C12P 13/04; C12P 13/06
[52] U.S. Cl. ......................... 435/106; 435/136; 435/116; 532/569
[58] Field of Search ............................ 532/569; 435/106, 435/136, 116

[56] References Cited

FOREIGN PATENT DOCUMENTS

| | | |
|---|---|---|
| 0 493 060 | 7/1992 | European Pat. Off. . |
| 0 590 857 | 4/1994 | European Pat. Off. . |
| 866488 | 4/1961 | United Kingdom . |
| 1 562 794 | 11/1975 | United Kingdom . |

OTHER PUBLICATIONS

Database WPI, Derwent Publications Ltd., abstract No. 94–221861., JP–A–06 157 439, Jun. 3 1994.

Database WPI, Derwent Publications Ltd., abstract No. 77–89596Y., SU–A–541 839, Feb. 2 1977.

Database WPI, Derwent Publications Ltd., abstract No. 74–61182V., SU–A–403 670, Mar. 27, 1974.

Database WPI, Derwent Publications Ltd., abstract No. 66–28489F., SU–A–188 397, priority date Sep. 26, 1964.

Patent Abstracts of Japan, Shingo et al., "Preparation of Vitamin P", 54101412. Aug. 10, 1979 Jan. 25, 1978, 53007769.

Patent Abstracts of Japan, Yosuke et al., "Production of Natural Vitamin K Condensate", 05155803, Jun. 22, 1993, Nov. 30, 1991, 03342164.

*Primary Examiner*—Irene Marx
*Attorney, Agent, or Firm*—Foley & Lardner

[57] ABSTRACT

A process for producing calcium D-pantothenate, which comprises bringing a solution containing D-pantothenic acid directly produced by microbial fermentation into contact with activated carbon to adsorb the D-pantothenic acid to the activated carbon, eluting the D-pantothenic acid with a hydrophilic organic solvent, neutralizing the eluate with an alkali agent containing calcium to precipitate calcium D-pantothenate, and collecting the calcium D-pantothenate.

6 Claims, 3 Drawing Sheets

MICROBIAL PROCESS FOR PRODUCING CALCIUM D-PANTOTHENATE

FIELD OF THE INVENTION

The present invention relates to a process for producing calcium D-pantothenate from a fermentation broth of D-pantothenic acid directly produced with a microorganism. Calcium D-pantothenate has been widely used as a vitamin in medicines, foods, feeds, etc.

BACKGROUND OF THE INVENTION

Conventional processes for producing calcium pantothenate can be classified roughly into chemical synthesis processes and direct fermentation processes. A chemical synthesis process widely used in industrial production comprises subjecting D,L-pantolactone synthesized from the starting compound isobutylaldehyde to optical resolution by a chemical or enzymatic method and condensing the resulting D-pantolactone with β-alanine calcium to obtain calcium D-pantothenate. As a direct fermentation method, JP-A 6-261772 has recently disclosed a novel process for directly producing D-pantothenic acid with a microorganism from a saccharide and β-alanine. In particular, it discloses a process for producing calcium D-pantothenate from a direct fermentation broth of D-pantothenic acid, which comprises subjecting the fermentation broth to desalting with ion-exchange chromatography, followed by neutralization to concentrate the D-pantothenic acid as a calcium salt, and adding methyl alcohol (methyl alcohol concentration: 83 v/v %) to precipitate crystals of calcium D-pantothenate.

Direct fermentation processes are more efficient than chemical synthesis processes because they require no optical resolution, etc. However, the fermentation broth contains insoluble materials such as microbial cells, etc., and various soluble impurities such as monosaccharides, oligosaccharides, organic acids, proteins, inorganic salts (cations, anions), etc., in addition to D-pantothenic acid. Therefore the most important problem has been how to efficiently separate and purify calcium D-pantothenate from the fermentation broth in high yield and purity. As described above, JP-A 6-261772 discloses a process for producing calcium D-pantothenate from a direct fermentation broth of D-pantothenic acid, which comprises subjecting the fermentation broth to desalting with ion-exchange chromatography, followed by neutralization to concentrate the D-pantothenic acid as a calcium salt, and adding methyl alcohol (methyl alcohol concentration: 83 v/v %) to precipitate crystals of calcium D-pantothenate. However, this process has the following drawbacks. (i) The treatment with an ion-exchange resin can not remove monosaccharides or oligosaccharides contained in the fermentation broth, and the crystallization raw solution contains them in an amount of about 10% based on pantothenic acid. These remaining monosaccharides or oligosaccharides cause coloring with heat during concentration of the ion-exchange resin treatment solution or a lowering of the crystallization yield during crystallization. (ii) In order to obtain high crystallization yield, the solution treated with ion-exchange resin must be concentrated to obtain a high concentration (about 50%) of calcium D-pantothenate before addition of methyl alcohol so that the concentration of calcium D-pantothenate in the crystallization raw solution becomes not less than 7 w/v% and the methyl alcohol concentration becomes about 90 v/v %. The calcium D-pantothenate solution in such concentration has a very high viscosity, which makes it difficult to concentrate the solution.

SUMMARY OF THE INVENTION

Figure 1:
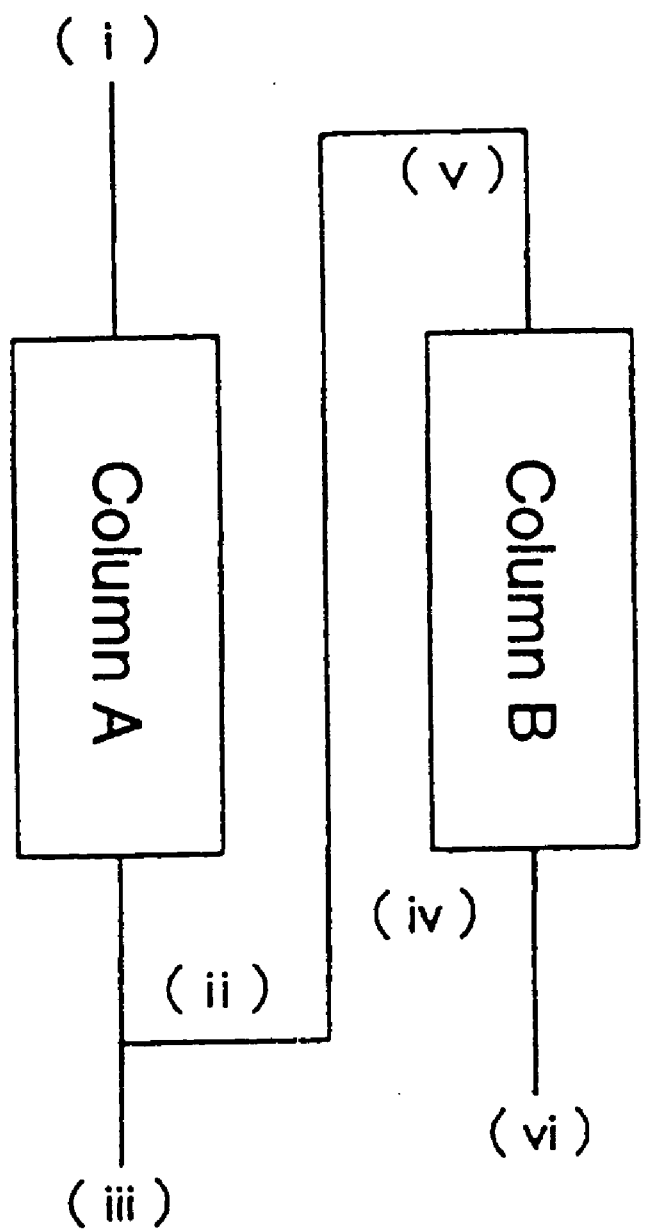
FIG. 1 is a diagram of a fixed bed in which Columns A and B packed with activated carbon are connected in series. The symbols (i) to (vi) represent passages.

The present inventors have intensively studied to obtain a process for efficiently producing good-quality calcium D-pantothenate in high yield from a culture solution containing saccharides, etc., in addition to D-pantothenic acid, which is obtained by a direct fermentation process. As a result, the present invention has been accomplished.

The present invention provides a process for producing calcium D-pantothenate, which comprises bringing a solution containing D-pantothenic acid directly produced by microbial fermentation into contact with activated carbon to adsorb the D-pantothenic acid to the activated carbon, eluting the D-pantothenic acid with a hydrophilic organic solvent, neutralizing the eluate with an alkali agent containing calcium to precipitate calcium D-pantothenate, and collecting the calcium D-pantothenate.

As described in detail below, the solution containing D-pantothenic acid is preferably a fermentation solution from which insoluble materials are removed. The pH of the solution containing D-pantothenic acid is preferably 1 to 5. Preferably, the solution containing D-pantothenic acid is continuously brought into contact with activated carbon packed in at least two columns connected in series until a saturated adsorption point. The hydrophilic organic solvent is preferably a lower alcohol having 1 to 5 carbon atoms, more preferably methyl alcohol. The alkali agent containing calcium is preferably calcium hydroxide. Preferably, the hydrophilic organic solvent is methyl alcohol, the alkali agent containing calcium is calcium hydroxide, and the calcium D-pantothenate is collected as crystals containing 4 molecules of methyl alcohol and one molecule of water.

DETAILED DESCRIPTION OF THE INVENTION

The solution containing D-pantothenic acid directly produced by microbial fermentation in the present invention can be obtained as disclosed in JP-A 6-261772 by cultivating a microorganism which can produce D-pantothenic acid, such as the intestinal bacterial strain *Escherichia coli* 814/pFV 31 (IFO 15374, FERM BP-4401), in a medium containing a saccharide source such as glucose, and bringing the bacterial strain into contact with β-alanine. At this time, the amount of the produced D-pantothenic acid is normally 40 g/L. It is preferred that insoluble solids such as bacterial cells are removed from the solution by conventional methods for removing insoluble materials in liquid, such as centrifugation, filtration, etc., to prevent contamination of carbon in the later treatment with activated carbon and prolong the life of the carbon, etc.

The solution containing D-pantothenic acid from which insoluble solids such as bacterial cells, etc., have been removed is adjusted to normally pH 1 to 5, preferably pH 2 to 4, with an inorganic acid such as hydrochloric acid, sulfuric acid, etc. When the pH is less than 1, D-pantothenic acid is readily decomposed, and its yield is decreased. When the pH exceeds 5, the amount of D-pantothenic acid adsorbed to activated carbon is reduced while that of saccharides is increased and the separability of saccharides is decreased.

The activated carbon to be used in the invention is not specifically limited. Any commercial activated carbon products for use in liquid-phase separations can be used. Preferred examples of the activated carbon include activated carbons in which the total pore volume of pores with a diameter of not more than 300 Å (hereinafter referred to as "pore volume") is not less than 0.4 cc/g and the average pore diameter of pores with a diameter of not more than 300 Å (hereinafter referred to as "average pore diameter") is not less than 17 Å. The activated carbons having such pore properties can be obtained, for example, by 1) soaking wood materials such as pieces of wood, coconut shells, etc., in a chemical such as zinc chloride, phosphoric acid, calcium chloride, etc., followed by sintering at about 600 to 700° C., and washing the chemical with an acid such as hydrochloric acid, etc., or 2) treating a mineral material such as coal, petroleum pitch, etc., with an alkali, followed by activation with steam, carbon dioxide gas, etc., at 750 to 900° C. The activated carbon may be in powder or granular forms. However, when it is packed in columns for use, it is preferably in granular forms from the viewpoint of column pressure control. Examples of the activated carbon include granular Shirasagi KLH (manufactured by Takeda Chemical Industries, Ltd., pore volume: 1.09 cc/g, average pore diameter: 32 Å), granular Sirasagi W (manufactured by Takeda Chemical Industries, Ltd., pore volume: 0.49 cc/g, average pore diameter: 18 Å), granular Sirasagi LH2C (manufactured by Takeda Chemical Industries, Ltd., pore volume: 0.74 cc/g, average pore diameter: 19 Å), CAL (manufactured by Calgon Corporation, pore volume: 0.55 cc/g, average pore diameter: 21 Å), granular activated carbon Daiahope 008 (manufacture by Mitsubishi Chemical Cooperation, pore volume: 0.61 cc/g, average pore diameter: 20 Å), etc.

The liquid to be treated is preferably brought into contact with activated carbon by the fixed-bed adsorption method in which the liquid to be treated is passed through activated carbon packed in a column. This method permits chromatographic separation of impurities and facilitates fractionation of the eluate of D-pantothenic acid with a hydrophilic organic solvent. A preferred method for practical use is the so-called series adsorption, in which the liquid to be treated is passed through at least two columns in series packed with activated carbon to adsorb D-pantothenic acid to the activated carbon.

Adsorption treatment using two columns is explained as an example below. As shown in FIG. 1, columns A and B packed with activated carbon are connected in series, and the liquid to be treated is passed through the columns in the following order: (i)–(ii)–(iv)–(v)–(vi). The flow is continued until the concentration of pantothenic acid at the outlet of Column A becomes the same as that at the inlet of Column A. Once the concentrations at the outlet and inlet become the same, Columns A and B are separated from each other, the flowing is switched to Column B, and another activated carbon column is connected in series to Column B. The flowing is continued until the concentrations of pantothenic acid at the outlet and inlet of Column B becomes the same.

Figure 2:
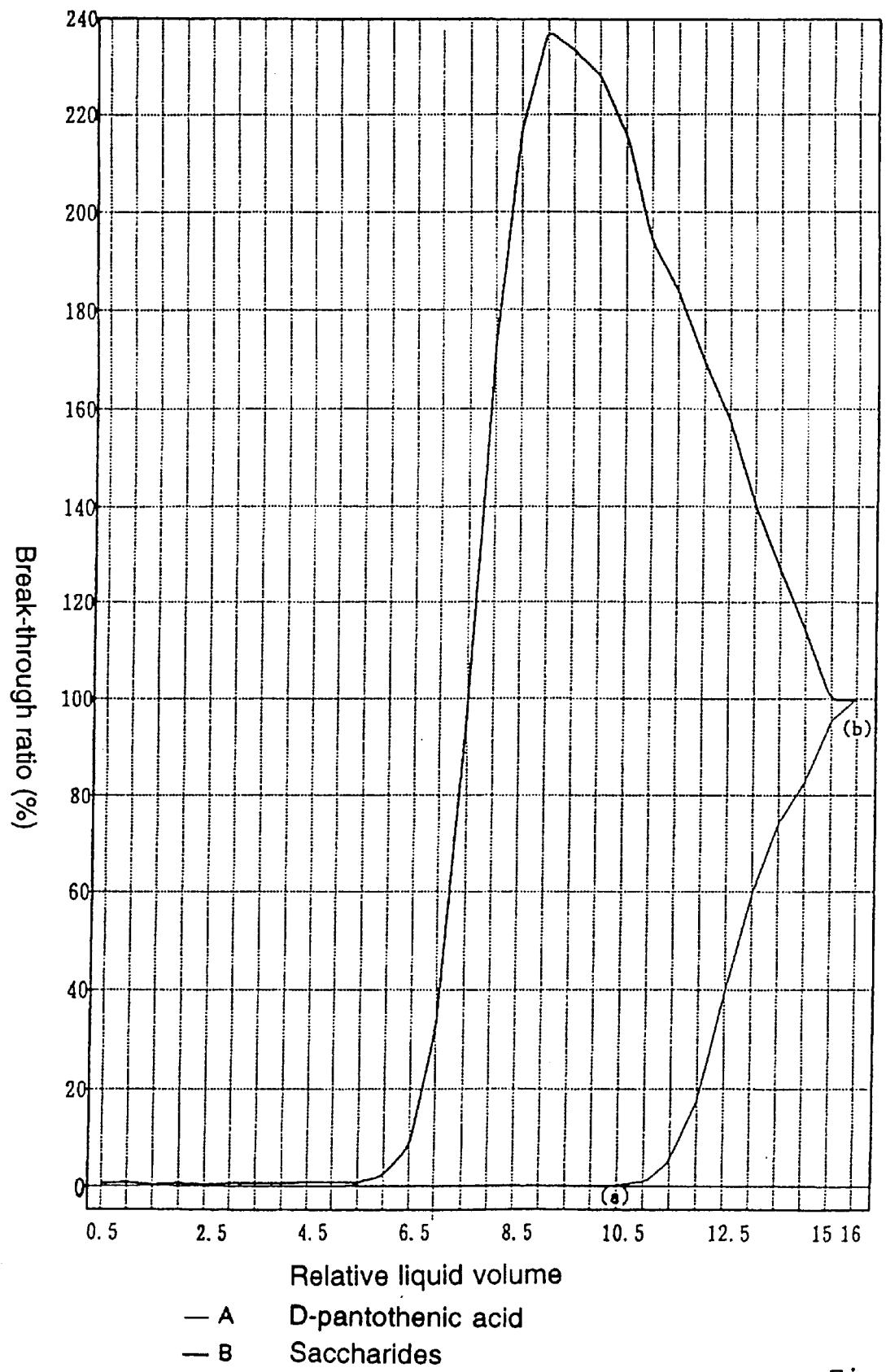
FIG. 2 shows break-through curves obtained when the liquid to be treated was passed through LH2C carbon column. The thin solid line A represents a break-through curve of D-pantothenic acid. The heavy solid line B represents a break-through curve of saccharides. (a) is a break-through adsorption point of D-pantothenic acid. (b) is a saturated adsorption point of D-pantothenic acid.

FIG. 2 shows break-through curves of D-pantothenic acid and saccharides when the direct fermentation broth which was previously subjected to bacterial cell separation, decolorized with activated carbon and adjusted to pH 3 with hydrochloric acid was passed through LH2C carbon column. The point at which the concentrations of pantothenic acid at the outlet and inlet of Column A become the same is the saturated adsorption point (b). At the saturated adsorption point (b), D-pantothenic acid is adsorbed (about 200 g/L–LH2C) in an amount of about 1.5 times that at the break-through adsorption point (a) where no pantothenic acid is leaked. The D-pantothenic acid leaked after the break-through adsorption point is adsorbed in the next column. Saccharides or other impurities coexisting in the liquid to be treated have lower adsorbability to D-pantothenic acid and are therefore forced to be eluted by D-pantothenic acid, and the break-through ratio of the saccharides or other impurities reaches 250%. It has been found that, when the treatment is continued to the saturated adsorption point, at least 90% of the saccharides in the liquid to be treated can be separated and removed. This is a novel finding unexpected to those skilled in the art. Inorganic salts contained in the liquid to be treated flow out to adsorption waste, because they do not adsorb to activated carbon. The inorganic salts can thus be separated and removed.

Then, D-pantothenic acid is eluted by passing a hydrophilic organic solvent through the activated carbon column in which D-pantothenic acid is saturatedly adsorbed. Preferred examples of the hydrophilic organic solvents include lower alcohols having 1 to 5 carbon atoms, such as methyl alcohol, ethyl alcohol, isopropyl alcohol, etc. In particular, methyl alcohol is preferred for the later crystallization step. That is, the crystals of calcium D-pantothenate have polymorphs and exist as $\alpha$, $\beta$ or $\gamma$ crystals, crystals having four molecules of methyl alcohol (MeOH) and one molecule of $H_2O$ (4MeOH•$1H_2O$ crystals) or amorphous forms depending on the solvent environment. Granular 4MeOH•$1H_2O$ crystals are crystallized from the crystallization raw solution when methyl alcohol is used as the crystallization solvent, and the separability is very high. The temperature for the elution is 10 to 30° C., preferably 20 to 30° C.

Figure 3:
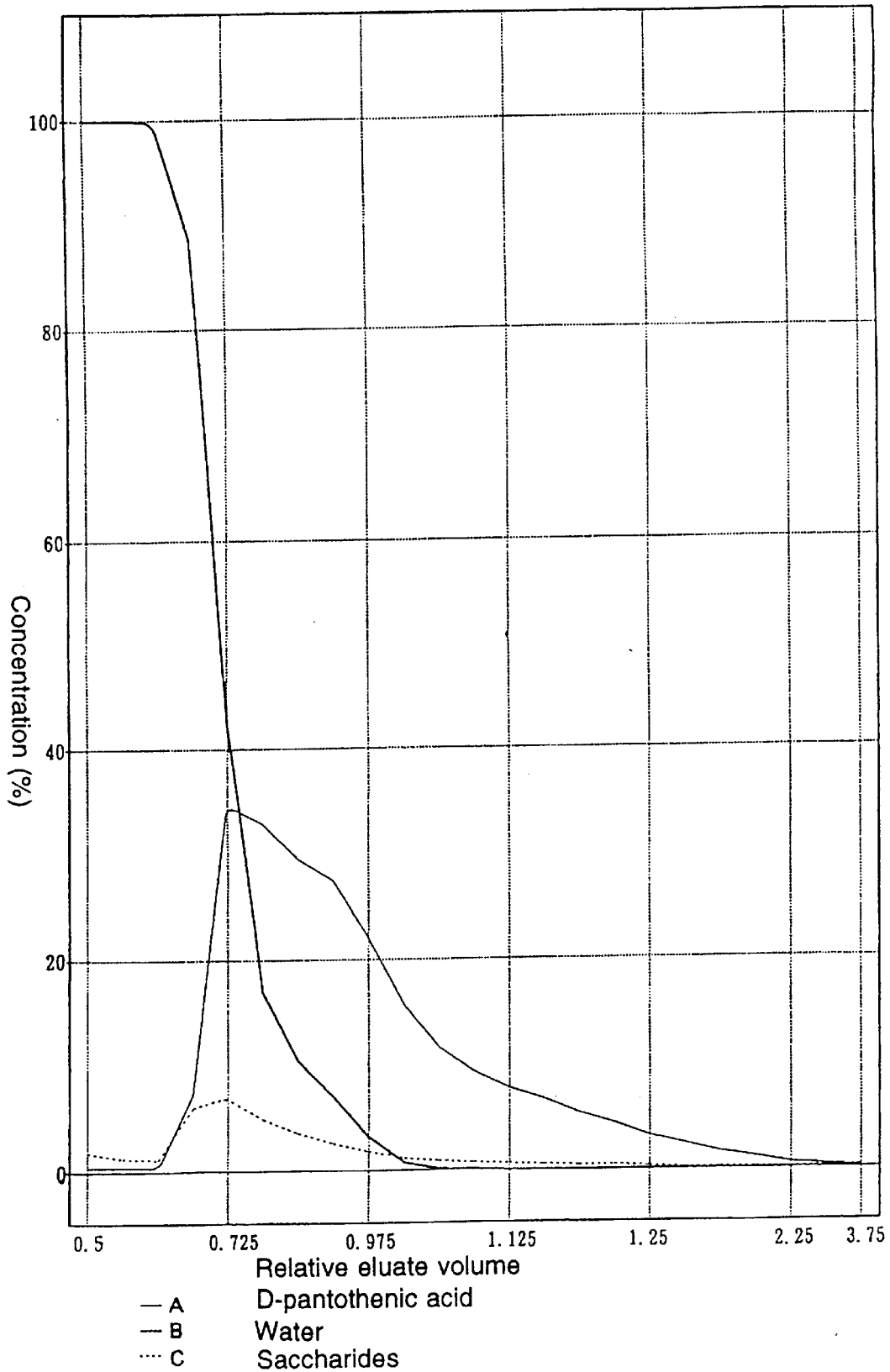
FIG. 3 shows elution curves obtained in the elution from LH2C carbon column using methyl alcohol as the eluant. The thin solid line A, the heavy solid line B, and the dotted line C represent elution curves of D-pantothenic acid, water, and saccharides, respectively.

The elution of D-pantothenic acid from an activated carbon column using methyl alcohol is explained below by referring to, for example, FIG. 3 showing elution curves in Example 1.

The first fraction (0.7 volume against LH2C carbon volume) contained water which was retained in the column and forced to be eluted. The concentration of D-pantothenic acid in this fraction was only 0.4 w/v %. The second fraction (1.5 volume) contained 8.7 w/v % of D-pantothenic acid and 7.5 w/v % of water. Since the concentration of D-pantothenic acid in the liquid to be treated was 2.6 w/v %, D-pantothenlc acid was concentrated 3.4-fold in this fraction. The last fraction (0.8 volume) contained 0.9 w/v % of D-pantothenic acid and 0.05 w/v % of water. The recoveries of D-pantothenic acid in three fractions were 2%, 90%, and 4%, respectively.

In view of the crystallization efficiency in the later crystallization, the concentration of the hydrophilic organic solvent in the eluate is normally 80 to 98 v/v %, preferably 85 to 95%, more preferably 90 to 92%, and the concentration of D-pantothenic acid is preferably not less than 7 w/v %. Therefore the above 1.5 volume of the eluted fraction can be neutralized to obtain the crystallization raw solution.

Then, the eluate is neutralized with an alkali agent containing calcium. Any alkali agent can be used so long as it contains calcium in a sufficient amount to neutralize D-pantothenic acid contained in the eluate. In particular, calcium hydroxide is preferred. In more practical uses, powdered calcium hydroxide in nearly equal moles to D-pantothenic acid is added to the eluate. When unreacted calcium hydroxide micropowder remains, it is preferred to filter it off. The liquid temperature during the neutralization is preferably kept at not less than 15° C. to avoid crystallization of calcium D-pantothenate.

After the crystallization raw solution thus prepared is cooled to not more than 10° C., preferably not more than 5° C., seed crystals are added in an amount of about 0.2 w/w % based on calcium D-pantothenate, and the mixture is allowed to stand for not less than 10 hours with stirring at 0 to 5° C. to obtain crystals of calcium D-pantothenate in high yield. The crystallization slurry is centrifuged with a conventional centrifugal dehydrator or filtered with a filter press to obtain wet crystals.

When methyl alcohol is used as the eluant, the wet crystals contain about 25 v/v % of methyl alcohol and about 5 v/v % of water. The wet crystals can be dried under reduced pressure at 70 to 80° C. to decrease the water content to about 0.5%. If necessary, the wet crystals can be dried using humidity-conditioned air (80° C., RH 20%) to control the water content to about 2%. In this manner, calcium D-pantothenate powder containing substantially no methyl alcohol can be obtained. Alternatively, the wet crystals are dissolved in water, the resulting solution is concentrated so that the concentration of calcium D-pantothenate becomes 50 w/v % by evaporating the solvent, and spray-dried with a conventional spray dryer to obtain calcium D-pantothenate powder. All of the crystal forms of the dried product have been converted to amorphous forms.

As described above, the process of the present invention is an very efficient process producing calcium D-pantothenate in high yield. In this process, a solution containing D-pantothenic acid is passed through an activated carbon column to saturatedly adsorb D-pantothenic acid to the activated carbon and at the same time effectively separate and remove inorganic ions and saccharides, and the D-pantothenic acid is eluted with a hydrophilic organic solvent such as an alcohol. If appropriate eluted fraction is selected in view of the solvent concentration and D-pantothenic acid concentration, the fraction per se can be used as the starting raw liquid for the neutralization and crystallization steps. In addition, calcium D-pantothenate can easily be separated and collected after crystallization.

EXAMPLES

The following examples further illustrate the present invention in detail but are not to be construed to limit the scope of the invention.

Example 1

*Escherichia coli* IFO 814/pFV 31 strain was cultivated by a conventional method in a medium containing glucose as a carbon source in a 5 liter jar fermentor to obtain a D-pantothenic acid direct fermentation broth (2.5 L). The fermentation broth was filtered through a ceramic filter (manufactured by Toshiba Ceramic) with a pore diameter of 0.1$\mu$ at 40° C. to obtain a filtrate (1.67 L) from which insoluble solids such as bacterial cells were removed. This filtrate contained D-pantothenic acid (38.5 mg/ml (64.3 g)), saccharides (total amount determined by the phenol-sulfuric acid method: 10.3 mg/ml (about 27% based on D-pantothenic acid)). This filtrate was passed through a column (inner diameter: 70 mm, height: 130 mm, packing volume: 500 ml) packed with activated carbon K-1 for decoloration (manufactured by Takeda Chemical Industries, Ltd., pore volume: 1.12 cc/g, average pore diameter: 32 Å) to obtain a liquid (2.4 L) (decoloration ratio: 99.5%) containing the water for the washing. Conc. hydrochloric acid (56 ml) was added to this liquid to adjust the pH to 3.0, and the liquid was passed continuously through two columns (Columns A and B, inner diameter: 50 mm, height: 100 mm, packing volume: 200 ml) connected in series and packed with activated carbon for liquid phase separation (LH2C carbon, granular, steam-activated carbon, manufactured by Takeda Chemical Industries, Ltd.). The amount of the raw liquid passed through Column A to the saturated adsorption point was 2.2 L. Column A adsorbed 29 g (145 g/L–LH2C carbon) of D-pantothenic acid by this operation. After the saturated adsorption point, Column A was separated from Column B. and the remaining liquid was passed through Column B. Column A was washed with 600 ml of water, and then D-pantothenic acid was eluted with methyl alcohol. The first 0.7 volume (140 ml) was discarded; and the second 1.5 volume (300 ml) was used in the later crystallization step. The last 0.8 volume (160 ml) was used as the eluent in the next column to recover D-pantothenic acid.

The concentrations of D-pantothenic acid, total saccharides, methyl alcohol in the second fraction were 8.7 w/v % (26.3 g), 0.43 w/v % (1.3 g) and 92.5 v/v %, respectively. To this fraction was added calcium hydroxide powder (4.8 g), and the mixture was stirred well. Thus, D-pantothenic acid was neutralized to obtain a calcium salt (calcium D-pantothenate: 28.6 g). The liquid was filtered through a Nutsche funnel pre-coated with diatomaceous earth. These operations were carried out at 20 to 25° C. The filtrate was used as the crystallization raw solution. The crystallization raw solution was transferred to a round-bottom flask equipped with a stirrer, and cooled to 5° C. Seed crystals (0.2 w/w % based on calcium D-pantothenate) were added, and the mixture was cooled to 2° C. and kept at the same temperature for 15 hours. In this manner, crystallization was carried out. The crystallization slurry was filtered through a 3 G glass filter, and methyl alcohol at 5° C. was sprayed for washing to obtain wet crystals (36.6 g) (calcium D-pantothenate: 34.4 g, crystallization yield: 90%) containing 4 molecules of MeOH (MeOH content: 26%) and one molecule of $H_2O$ (water content: 4%). The wet crystals were subjected to conventional drying under reduced pressure at 80° C and drying with humidity-conditioned air (80° C., RH 20%) to obtain dried powders (26.1 g, water content: 2.4%) of calcium D-pantothenate. This product meets the Japanese, U.S. and U.K. standards with respect to the clarity, color, calcium content, nitrogen content, specific rotation, crystal forms, etc.

As described above, the process of the present invention can efficiently remove impurities, in particular saccharides, by bringing a solution containing D-pantothenic acid directly produced by microbial fermentation into contact with activated carbon to saturatedly adsorb D-pantothenic acid to the activated carbon. Subsequent elution with a hydrophilic organic solvent such as methyl alcohol, etc., followed by crystallization can provide good-quality calcium D-pantothenate from the fermentation filtrate in high yield and very efficiently.

We claim:

1. A process for producing calcium D-pantothenate, comprising:

removing insoluble solids from a fermentation broth of D-pantothenic acid directly produced by microbial fermentation;

decolorizing the fermentation broth with activated carbon to obtain a solution containing D-pantothenic acid;

adjusting the pH of the solution containing D-pantothenic acid to 1 to 5;

bringing the solution containing D-pantothenic acid into contact with granular activated carbon to which saccharides have lower adsorbability than D-pantothenic acid and which is packed in at least two columns connected in series continuously to adsorb the D-pantothenic acid to the activated carbon until the saturated adsorption point;

eluting the D-pantothenic acid with a hydrophilic organic solvent;

neutralizing the eluate with an alkali agent containing calcium to precipitate calcium D-pantothenate; and collecting the calcium D-pantothenate.

2. The process according to claim 1, wherein the hydrophilic organic solvent is a lower alcohol having 1 to 5 carbon atoms.

3. The process according to claim 2, wherein the lower alcohol is methyl alcohol.

4. The process according to claim 1, wherein the alkali agent containing calcium is calcium hydroxide.

5. The process according to claim 1, wherein the hydrophilic organic solvent is methyl alcohol, the alkali agent containing calcium is calcium hydroxide, and the calcium D-pantothenate is collected as crystals containing 4 molecules of methyl alcohol and one molecule of water.

6. The process according to claim 1, wherein the activated carbon is granular steam-activated carbon.

* * * * *

UNITED STATES PATENT AND TRADEMARK OFFICE
CERTIFICATE OF CORRECTION

PATENT NO. : 6,013,492
DATED : January 11, 2000
INVENTOR(S) : Sunao NISHIMURA, et al..

It is certified that error appears in the above-identified patent and that said Letters Patent is hereby corrected as shown below:

Please note on the front cover of the patent

Item [86], § 371 Date: June 4, 1996 and § 102(e) Date: June 4, 1996, should read - - 371 Date: June 5, 1996 and § 102(e) Date: June 5, 1996- -.

Signed and Sealed this

Seventeenth Day of April, 2001

Attest:

NICHOLAS P. GODICI

Attesting Officer    Acting Director of the United States Patent and Trademark Office